United States Patent [19]

Berg

[11] Patent Number: 4,980,033

[45] Date of Patent: Dec. 25, 1990

[54] RECOVERY OF TRIETHYLENE GLYCOL FROM TRIOLS BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 577,323

[22] Filed: Sep. 4, 1990

[51] Int. Cl.⁵ .................. B01D 3/36; C07C 41/42
[52] U.S. Cl. ..................... 203/62; 203/68; 203/69; 568/621; 568/868; 568/869
[58] Field of Search .................. 203/68, 69, 62; 568/621, 869, 868, 623

[56] References Cited

U.S. PATENT DOCUMENTS

| | | | |
|---|---|---|---|
| 2,865,819 | 12/1958 | Hagemeyer et al. | 203/69 |
| 3,809,724 | 5/1974 | Golden | 203/69 |
| 3,847,754 | 11/1974 | Oliver | 568/621 |
| 3,859,368 | 1/1975 | Kollar | 203/68 |
| 4,021,311 | 5/1977 | Becker | 203/69 |
| 4,057,471 | 11/1977 | Chueh | 203/69 |
| 4,655,879 | 4/1987 | Brockmann et al. | 568/869 |

Primary Examiner—Wilbur Bascomb

[57] ABSTRACT

Triethylene glycol cannot be easily separated from glycerine or 1,2,4-butanetriol by atmospheric or reduced pressure distillation because of the closeness of their boiling points. Triethylene glycol can be readily separated from glycerine or 1,2,4-butanetriol by azeotropic distillation. Effective agents are p-xylene, alphapinene and diisobutyl ketone.

1 Claim, No Drawings

RECOVERY OF TRIETHYLENE GLYCOL FROM TRIOLS BY AZEOTROPIC DISTILLATION

This is a revision of appl. Ser. No. 07/507,033, Abandoned.

FIELD OF THE INVENTION

This invention relates to a method for separating triethylene glycol from glycerine and/or 1,2,4-butanetriol using certain organic compounds as the agent in azeotropic distillation.

DESCRIPTION OF PRIOR ART

Azeotropic distillation is the method of separating close boiling compounds from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azetrope forming agent and the more volatile component are taken off as overhead product and the less volatile component comes off as bottoms product. The usual methods of separating the azeotrope former from the more volatile component are cooling and phase separation or solvent extraction.

In the hydrocracking of higher carbohydrates such as glucose, sorbitol or sucrose, the molecule is broken into fragments of lower molecular weight to form compounds which belong to the glycol or polyol family. Some of the resulting polyols boil so close to one another that their separation by ordinary rectification is difficult. The relative volatility is so low that a large number of theoretical plates are required to produce high purity polyols.

For instance, three of the close boiling polyols encountered in this process are triethylene glycol, b.p.=285° C., glycerine, b.p.=290° C. and 1,2,4-butanetriol, b.p.=190/18 mm.

TABLE 1

Plates Required To Effect Separation In 99% Purity

| Relative Volatility | Theoretical Plates | Actual Plates, 75% Efficiency |
|---|---|---|
| 1.25 | 41 | 55 |
| 1.35 | 31 | 42 |
| 1.45 | 25 | 34 |
| 1.50 | 23 | 31 |
| 1.70 | 18 | 24 |
| 1.80 | 16 | 21 |

The difficulty of separating these one from another by rectification can be shown by the data presented in Table 1. Table 1 shows that rectification of triethylene glycol from glycerine in 99% purity requires 55 actual plates. Using azeotropic distillation with an agent yielding a relative volatility of 1.8 would require only 21 actual plates. Thus, azeotropic distillation would be an attractive method of effecting the separation of these two polyols if agents can be found that (1) will increase the relative volatility of triethylene glycol to glycerine and (2) are easy to recover from the triethylene glycol.

Azeotropic distillation typically requires from one to five parts as much agent as triethylene glycol being boiled up in the column which increases the heat requirement as well as larger diameter plates to accomodate the increased liquid and vapor in the column.

The catalytic hydrocracking of sorbitol gave a mixture of polyols having the composition shown in Table 2.

TABLE 2

Polyols Produced By Hydrocracking Of Sorbitol

| Compound | Weight Percent | Boiling Point, °C. |
|---|---|---|
| 2,3-Butanediol | 3.5 | 182 |
| Propylene glycol | 16.5 | 187 |
| 1,2-Butanediol | 2.0 | 192 |
| Ethylene glycol | 25.2 | 198 |
| 1,3-Butanediol | 2.7 | 206 |
| 2,3-Hexanediol | — | 206 |
| 1,2-Pentanediol | — | 210 |
| 1,4-Pentanediol | — | 220 |
| 1,4-Butanediol | 2.1 | 230 |
| 1,5-Pentanediol | 0.1 | 242 |
| Diethylene glycol | 2.2 | 245 |
| 1,6-Hexanediol | — | 250 |
| Triethylene glycol | 2.1 | 285 |
| Glycerine | 38.8 | 290 |
| 1,2,4-Butanetriol | 4.8 | 190/18 mm. |
|  | 100.0 |  |

The principal products were 16.5% propylene glycol, 25.2% ethylene glycol and 38.8% glycerine. To be of commercial value in most uses, these compounds must be of high purity. Table 2 shows the other polyols that resulted are 3% 2,3-butanediol, 2%.1,2-butanediol, 2.7% 1,3-butanediol, 2.1% 1,4-butanediol, 0.1% 1,5-pentanediol, 2.2% diethylene glycol, 2.1% triethylene glycol and 4.8% 1,2,4-butanetriol. Table 2 also shows how close these minor polyols boil to propylene glycol, ethylene glycol and glycerine. When this mixture was subjected to rectification, either at one atm. or at reduced pressure, separation to high purity compounds could not be attained.

OBJECTIVE OF THE INVENTION

The objective of this invention is to provide a process or method of azeotropic distillation that will enhance the relative volatility of triethylene glycol to glycerine and 1,2,4-butanetriol in their separation in a column. It is a further object of this invention to identify organic compounds which in addition to the above constraints, are stable, can be separated from the triethylene glycol and can be recycled to the azeotropic distillation and reused with little decomposition.

SUMMARY OF THE INVENTION

The objects of this invention are provided by a process for separating triethylene glycol from glycerine and 1,2,4-butanetriol which entails the use of certain organic compounds in an azeotropic distillation process.

DETAILED DESCRIPTION OF THE INVENTION

I have discovered that certain organic compounds will effectively enhance the relative volatility in azeotropic distillation of triethylene glycol from glycerine and 1,2,4-butanetriol when they occur as a close boiling mixture. In the mixture of polyols shown in Table 2, the major products are propylene glycol, ethylene glycol and glycerine. To be of commercial value, these compounds must be obtained in high purity.

Triethylene glycol and 1,2,4-butanetriol are the polyols boiling closest to glycerine, see Table 1. Tables 3 and 4 list the agents found to be effective in separating triethylene glycol from these two triols. The 1,2,4-butanetriol boils so much higher than triethylene glycol that it poses no difficulty in separation. The relative volatility is too high to be measured accurately. p-Xylene, ethylbenzene, cumene and alpha-pinene bring the triethylene glycol out as two-phase overhead. 2,6-Dimethyl-4-heptanone and diisobutyl ketone bring the triethylene glycol out as a single phase overhead.

TABLE 3

| Agent | Azeo. Temp. | Time hrs. | OVERHEAD | | | BOTTOMS | | | % TEG in Overhead | Relative Volatility TEG:Gly |
|---|---|---|---|---|---|---|---|---|---|---|
| | | | % TEG | % Gly | % 124 Bu | % TEG | % Gly | % 124 Bu | | |
| Alpha-Pinene | 103 | 2 | 99.1 | 0.9 | — | 96 | 4 | — | 40 | 4.9 |
| 2,6-Dimethyl-4-heptanone | 112 | 4 | 3.5 | 96.5 | — | 2.8 | 97.2 | — | 10 | 1.2 |

Effective Agents For Separating Triethylene Glycol From Both Glycerine And 1,2,4-Butanetriol

TABLE 4

Data From Vapor-Liquid Equilibrium Still

| Agent | Relative Volatility | |
|---|---|---|
| | TEG:Gly | TEG:1,2,4-Bu |
| Ethylbenzene | 2.1 | 31 |
| p-Xylene | 3.6 | 3 |
| Cumene | 1.8 | 23 |
| Diisobutyl ketone | 1.7 | 3.1 |

WORKING EXAMPLES

Example 1

Twenty grams of triethylene glycol, 20 grams of glycerine, 5 grams of 1,2,4-butanetriol and 40 grams of diisobutyl ketone were charged to the vapor-liquid equilibrium still and refluxed for three hours. The vapor composition was 58.3% triethylene glycol, 21.2% glycerine and 0.5% 1,2,4-butanetriol and the liquid composition was 66.7% triethylene glycol, 31% glycerine and 2.3% 1,2,4-butanetriol which is a relative volatility of triethylene glycol to glycerine of 1.7 and of glycerine to 1,2,4-butanetriol of 3.1.

Example 2

Thirty grams of triethylene glycol, 10 grams of glycerine and 100 grams of alpha-pinene were placed in the stillpot of a 30 theoretical plate helices packed rectification column and refluxed for two hours. The overhead condensed into two layers comprising 60% alpha-pinene and 40% triethylene glycol - glycerine. Analysis by gas chromatography indicated an overhead composition of the polyol layer of 99.1% triethylene glycol, 0.9% glycerine and a stillpot composition of 96% triethylene glycol, 4% glycerine which is a relative volatility of 4.9.

I claim:

1. A method for recovering triethylene glycol from a mixture of triethylene glycol, glycerine and 1,2,4-butanetriol which comprises distilling a mixture of triethylene glycol, glycerine and 1,2,4-butanetriol in a rectification column in the presence of an azeotrope forming agent, recovering the triethylene glycol and the azeotrope forming agent as overhead product and obtaining the glycerine and the 1,2,4-butanetriol from the stillpot, wherein said azeotrope forming agent consists of one material selected from the group consisting of p-xylene, alpha-pinene, ethyl benzene, cumene, diisobutyl ketone and 2,6-dimethyl-4-heptanone.

* * * * *